(12) United States Patent
McGuckin, Jr.

(10) Patent No.: US 8,834,551 B2
(45) Date of Patent: Sep. 16, 2014

(54) VASCULAR DEVICE WITH VALVE FOR APPROXIMATING VESSEL WALL

(75) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 297 days.

(21) Appl. No.: 12/221,911

(22) Filed: Aug. 7, 2008

(65) Prior Publication Data

US 2009/0062901 A1 Mar. 5, 2009

Related U.S. Application Data

(60) Provisional application No. 60/967,227, filed on Aug. 31, 2007.

(51) Int. Cl.
*A61F 2/06* (2013.01)
*A61F 2/84* (2006.01)
*A61F 2/24* (2006.01)

(52) U.S. Cl.
CPC ....... *A61F 2/2418* (2013.01); *A61F 2220/0016* (2013.01); *A61F 2/2475* (2013.01); *A61F 2/2436* (2013.01); *A61F 2/2427* (2013.01)
USPC .......................... 623/1.11; 623/1.24; 623/1.36

(58) Field of Classification Search
CPC ........... A61F 2/07; A61F 2/95; A61F 2/2418; A61F 2/2427; A61F 2/2436; A61F 2/2439
USPC .................. 623/1.23, 1.26, 1.11, 1.13, 2.11
See application file for complete search history.

(56) References Cited

U.S. PATENT DOCUMENTS

| | | | |
|---|---|---|---|
| 4,275,469 A | 6/1981 | Gabbay | |
| 4,759,758 A | 7/1988 | Gabbay | |
| 5,019,102 A | 5/1991 | Hoene | |
| 5,147,389 A | 9/1992 | Lane | |
| 5,151,105 A * | 9/1992 | Kwan-Gett | ............. 623/1.32 |
| 5,258,022 A | 11/1993 | Davidson | |
| 5,350,398 A | 9/1994 | Pavenik et al. | |
| 5,358,518 A | 10/1994 | Camilli | |
| 5,375,612 A | 12/1994 | Cottenceau et al. | |
| 5,395,390 A | 3/1995 | Simon et al. | |
| 5,397,351 A | 3/1995 | Pavenik et al. | |
| 5,397,355 A | 3/1995 | Marin | |

(Continued)

FOREIGN PATENT DOCUMENTS

| | | |
|---|---|---|
| DE | 19857887 | 7/2000 |
| EP | 1894543 | 3/2008 |

(Continued)

*Primary Examiner* — Kathleen Holwerda
*Assistant Examiner* — Sarah W Aleman
(74) *Attorney, Agent, or Firm* — Neil D. Gershon (57) ABSTRACT

A vascular device comprising a body movable from a collapsed insertion position to an expanded position having a larger cross-sectional dimension. The body includes a plurality of struts. At least two elongated struts extend distally from the body. A plurality of vessel engaging members extend outwardly from the body for engaging the internal wall of a vessel. A valve is movable between a collapsed delivery position and an expanded placement position, wherein at least a portion of the valve extends distally from the body in the delivery and placement positions and the elongated struts engage a distal portion of the valve in the placement position of the valve to retain the valve.

20 Claims, 11 Drawing Sheets

(56) References Cited

U.S. PATENT DOCUMENTS

| | | | | |
|---|---|---|---|---|
| 5,411,552 | A | 5/1995 | Anderson | |
| 5,443,500 | A | 8/1995 | Sigwart | |
| 5,500,014 | A | 3/1996 | Quijano et al. | |
| 5,540,712 | A | 7/1996 | Kleshinski et al. | |
| 5,545,210 | A | 8/1996 | Hess et al. | |
| 5,562,728 | A | 10/1996 | Lazarus | |
| 5,591,197 | A | 1/1997 | Orth | |
| 5,593,417 | A | 1/1997 | Rhodes | |
| 5,609,598 | A | 3/1997 | Laufer | |
| 5,643,278 | A | 7/1997 | Wijay | |
| 5,674,279 | A | 10/1997 | Wright | |
| 5,746,766 | A | 5/1998 | Edoga | |
| 5,792,155 | A | 8/1998 | Van Cleef | |
| 5,800,526 | A | 9/1998 | Anderson et al. | |
| 5,810,847 | A | 9/1998 | Laufer et al. | |
| 5,827,322 | A | 10/1998 | Williams | |
| 5,840,081 | A | 11/1998 | Andersen et al. | |
| 5,843,164 | A | 12/1998 | Frantzen et al. | |
| 5,855,601 | A | 1/1999 | Bessler et al. | |
| 5,876,434 | A | 3/1999 | Flomenblit et al. | |
| 5,885,258 | A | 3/1999 | Sachdeva et al. | |
| 5,902,317 | A | 5/1999 | Kleshinski et al. | |
| 5,957,949 | A | 9/1999 | Leonhardt et al. | |
| 6,004,347 | A | 12/1999 | McNamara et al. | |
| 6,004,348 | A | 12/1999 | Banas et al. | |
| 6,014,589 | A | 1/2000 | Farley et al. | |
| 6,027,525 | A | 2/2000 | Suh et al. | |
| 6,033,398 | A | 3/2000 | Farley et al. | |
| 6,036,687 | A | 3/2000 | Laufer et al. | |
| 6,042,606 | A | 3/2000 | Frantzen | |
| 6,053,896 | A | 4/2000 | Wilson et al. | |
| 6,071,277 | A | 6/2000 | Farley et al. | |
| 6,080,160 | A | 6/2000 | Chen et al. | |
| 6,086,610 | A | 7/2000 | Duerig et al. | |
| 6,120,534 | A | 9/2000 | Ruiz | |
| 6,129,758 | A | 10/2000 | Love | |
| 6,136,025 | A | 10/2000 | Barbut et al. | |
| 6,139,536 | A | 10/2000 | Mikus et al. | |
| 6,149,660 | A | 11/2000 | Laufer et al. | |
| 6,162,245 | A | 12/2000 | Jayaraman | |
| 6,179,878 | B1 | 1/2001 | Duerig et al. | |
| 6,200,336 | B1 | 3/2001 | Pavcnik et al. | |
| 6,221,102 | B1 | 4/2001 | Baker et al. | |
| 6,224,626 | B1 | 5/2001 | Steinke | |
| 6,231,561 | B1 | 5/2001 | Frazier et al. | |
| 6,254,564 | B1 | 7/2001 | Wik et al. | |
| 6,258,118 | B1 | 7/2001 | Baum et al. | |
| 6,287,339 | B1 | 9/2001 | Vazquez et al. | |
| 6,290,721 | B1 | 9/2001 | Heath | |
| 6,299,636 | B1 | 10/2001 | Schmitt et al. | |
| 6,299,637 | B1 | 10/2001 | Shaolian et al. | |
| 6,302,917 | B1 | 10/2001 | Dua et al. | |
| 6,309,416 | B1 | 10/2001 | Swanson et al. | |
| 6,425,915 | B1 | 7/2002 | Khosravi et al. | |
| 6,440,163 | B1 | 8/2002 | Swanson et al. | |
| 6,454,799 | B1 * | 9/2002 | Schreck | 623/2.18 |
| 6,503,272 | B2 | 1/2003 | Duerig et al. | |
| 6,511,491 | B2 | 1/2003 | Grudem et al. | |
| 6,527,800 | B1 | 3/2003 | McGuckin et al. | |
| 6,572,646 | B1 | 6/2003 | Boylan et al. | |
| 6,582,461 | B1 | 6/2003 | Burmeister et al. | |
| 6,626,899 | B2 | 9/2003 | Houser et al. | |
| 6,635,080 | B1 | 10/2003 | Lauterjung et al. | |
| 6,685,739 | B2 | 2/2004 | DiMatteo | |
| 6,695,878 | B2 | 2/2004 | McGuckin et al. | |
| 6,733,525 | B2 * | 5/2004 | Yang et al. | 623/2.18 |
| 6,740,111 | B1 | 5/2004 | Lauterjung | |
| 7,007,698 | B2 | 3/2006 | Thornton | |
| 7,018,387 | B2 | 3/2006 | Suyker et al. | |
| 7,041,128 | B2 | 5/2006 | McGuckin et al. | |
| 2001/0005787 | A1 | 6/2001 | Oz et al. | |
| 2002/0002401 | A1 | 1/2002 | McGuckin et al. | |
| 2002/0032481 | A1 * | 3/2002 | Gabbay | 623/2.11 |
| 2002/0055772 | A1 * | 5/2002 | McGuckin et al. | 623/1.24 |
| 2002/0138129 | A1 | 9/2002 | Armstrong et al. | |
| 2003/0018294 | A1 | 1/2003 | Cox | |
| 2003/0199987 | A1 | 10/2003 | Berg et al. | |
| 2004/0098098 | A1 | 5/2004 | McGuckin, Jr. et al. | |
| 2004/0220593 | A1 | 11/2004 | Greenhalgh | |
| 2005/0049692 | A1 | 3/2005 | Numamoto et al. | |
| 2006/0122692 | A1 | 6/2006 | Gilad et al. | |
| 2006/0149360 | A1 | 7/2006 | Schwammenthal et al. | |
| 2006/0190074 | A1 * | 8/2006 | Hill et al. | 623/1.23 |
| 2007/0112423 | A1 | 5/2007 | Chu | |
| 2008/0221669 | A1 | 9/2008 | Camilli et al. | |
| 2011/0202127 | A1 | 8/2011 | Mauch et al. | |

FOREIGN PATENT DOCUMENTS

| | | |
|---|---|---|
| WO | WO9740755 | 11/1997 |
| WO | WO9819629 | 5/1998 |
| WO | WO9956655 | 11/1999 |
| WO | 0149213 | 7/2001 |
| WO | WO02100297 | 12/2002 |
| WO | 2006004679 | 1/2006 |
| WO | WO2007067942 | 6/2007 |

* cited by examiner

FIG_1

FIG_3A

FIG_3B

FIG_3C

FIG. 14

VASCULAR DEVICE WITH VALVE FOR APPROXIMATING VESSEL WALL

This application claims priority to provisional application No. 60/967,227, filed Aug. 31, 2007, the entire contents of which are incorporated herein by reference.

BACKGROUND

1. Technical Field

This application relates to a vascular device and more particularly to a vascular device for approximating the vessel wall and placing a valve for treating venous valve insufficiency.

2. Background of Related Art

Veins in the body transport blood to the heart and arteries carry blood away from the heart. The veins have one-way valve structures in the form of leaflets disposed annularly along the inside wall of the vein which open to permit blood flow toward the heart and close to prevent back flow. That is, when blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to prevent blood flow in the opposite, i.e. retrograde, direction after the pressure is relieved. The leaflet structures, when functioning properly, extend radially inwardly toward one another such that the tips contact each other to block backflow of blood.

In the condition of venous valve insufficiency, the valve leaflets do not function properly as they thicken and lose flexibility, resulting in their inability to extend sufficiently radially inwardly to enable their tips to come into sufficient contact with each other to prevent retrograde blood flow. The retrograde blood flow causes the buildup of hydrostatic pressure on the residual valves and the weight of the blood dilates the wall of the vessel. Such retrograde blood flow, commonly referred to as reflux, leads to swelling and varicose veins, causing great discomfort and pain to the patient. Such retrograde blood flow, if left untreated can also cause venous stasis ulcers of the skin and subcutaneous tissue. There are generally two types of venous valve insufficiency: primary and secondary. Primary venous valve insufficiency is typically a condition from birth, where the vein is simply too large in relation to the leaflets so that the leaflets cannot come into adequate contact to prevent backflow. More common is secondary venous valve insufficiency which is caused by clots which gel and scar, thereby changing the configuration of the leaflets, i.e. thickening the leaflets creating a "stub-like" configuration. Venous valve insufficiency can occur in the superficial venous system, such as the saphenous veins in the leg, or in the deep venous system, such as the femoral and popliteal veins extending along the back of the knee to the groin.

A common method of treatment of venous valve insufficiency is placement of an elastic stocking around the patient's leg to apply external pressure to the vein, forcing the walls radially inwardly to force the leaflets into apposition. Although sometimes successful, the tight stocking is quite uncomfortable, especially in warm weather, as the stocking must be constantly worn to keep the leaflets in apposition. The elastic stocking also affects the patient's physical appearance, thereby potentially having an adverse psychological affect. This physical and/or psychological discomfort sometimes results in the patient remove the stocking, thereby preventing adequate treatment.

Another method of treatment has been developed to avoid the discomfort of the stocking. This method involves major surgery requiring the implantation of a cuff internally of the body, directly around the vein. This surgery requires a large incision, resulting in a long patient recovery time, scarring and carries the risks, e.g. anesthesia, inherent with surgery.

Another invasive method of surgery involves selective repairing of the valve leaflets, referred to as valvuloplasty. In one method, sutures are utilized to bring the free edges of the valve cusp into contact. This procedure is complicated and has the same disadvantages of the major surgery described above.

Commonly assigned U.S. Pat. Nos. 6,695,878 and 6,527,800, the entire contents of which are incorporated herein by reference as noted above, disclose an advantageous method and device to minimally invasively treat venous valve insufficiency without requiring an outer stocking or internal cuff. Such device avoids the physical and psychological discomfort of an external stocking as well as avoids the risk, complexity and expense of surgically implanted cuffs. The device is advantageously inserted minimally invasively, i.e. intravascularly, and functions to effectively bring the valve leaflets into apposition. This device first expands against the vessel wall to grasp the wall, and then contracts to bring the vessel wall radially inwardly so the leaflets can be pulled closer together to a functional position.

The vascular device of commonly assigned U.S. Pat. No. 6,676,698, the entire contents of which is incorporated by reference, utilizes the device of these foregoing applications for bringing the vessel wall radially inwardly to correct the dilation of the wall, but rather than rely on the patient's existing valve leaflets which may be scarred or non-functional, contains a replacement valve as a substitute for the patient's leaflets. Thus, advantageously, venous valve insufficiency can be treated minimally invasively by bringing the vessel wall inwardly and replacing the patient's valve.

It would be beneficial to provide additional retention structure for such devices. Additionally, it would be beneficial to minimize the insertion dimension of the device, thereby reducing the incision size to maximize the advantages of minimally invasive surgery.

SUMMARY OF THE INVENTION

The present application provides a vascular device comprising a body having a proximal portion and a distal portion and movable from a collapsed insertion position to an expanded position having a larger cross-sectional dimension. The body includes a plurality of struts. At least two elongated struts extend distally from the body and a plurality of vessel engaging members extend outwardly from the body for engaging the internal wall of a vessel. A valve is movable between a collapsed delivery position and an expanded placement position, wherein at least a portion of the valve extends distally from the body in the delivery and placement positions and the elongated struts engage a distal portion of the valve in the placement position of the valve to retain the valve.

Preferably, the vessel engaging members pull the internal wall of the vessel radially inwardly.

In one embodiment, the body is composed of shape memory material and the expanded position substantially corresponds to a memorized position of the body, and the body is further expanded to a second expanded position by an expandable member, and subsequently the body returns toward its memorized position.

Preferably, in the collapsed position, the elongated struts extend external to at least a proximal portion of the valve. In one embodiment, in the collapsed position, a distal end of elongated struts extends over a distal edge of the valve. In another embodiment, the valve includes at least two openings and in the placement position, a portion of the elongated struts extends through the openings in the valve.

In one embodiment, upon exposure of the valve from a delivery sheath, a portion of the valve is pulled proximally toward the body.

The device may include an expandable ring positioned within the valve, wherein in the insertion position the ring is in a collapsed position.

The present application also provides a vascular device comprising a body having a proximal portion and a distal portion, a valve extending distally from the body, and a retraction member connected to the valve. The body and valve are movable between a collapsed insertion position within a delivery sheath to an expanded placement position exposed from the delivery sheath, the body and valve having a larger cross-sectional dimension in the placement position. Upon exposure from the sheath, the retraction member applies a retraction force to the valve to pull the valve in a proximal direction.

In one embodiment, the retraction member comprises at least one shape memory wire.

In a preferred embodiment, the device includes at least two elongated members extending distally of the body, wherein the elongated members are preferably external to the valve as the valve is pulled proximally by the retraction member. In one embodiment, the elongated members engage a distal portion of the valve to retain the valve. In one embodiment, at least one of the elongated members is attached to the valve. In another embodiment, the valve has a plurality of openings, wherein upon retraction of the valve, the elongated members extend through the openings in the valve The device can further include an expandable ring contained within the valve wherein the expandable ring applies a radial force to the valve to force the valve against a vessel wall.

In one embodiment, a distal portion of the elongated members extend radially inwardly toward a longitudinal axis of the valve.

In one embodiment, the body is composed of a shape memory material and is expandable first to a memorized condition in response to exposure to body temperature and subsequently expanded to the expanded position by an expandable member.

The present invention also provides a method for treating venous valve insufficiency comprising:

inserting into a target vessel adjacent the region of the removed portion of valve leaflets a delivery device and a vascular device in an insertion position within the delivery device, the vascular device including a body, a plurality of vessel engaging members extending from the body, a valve, and a retraction member connected to the valve, wherein in the insertion position the body, retraction member and valve are in a reduced transverse dimensional configuration with at least a portion of the valve positioned distal of the body; and exposing the vascular device from the delivery device, wherein the exposure enables the retraction member to move the valve in a proximal direction and the exposure enables the body to expand to enable the vessel engaging members to engage the internal wall of the vessel.

Preferably, in the insertion position, at least a portion of the retraction member is positioned proximal of the valve. Preferably, in the insertion position the vascular device has a first overall length and after the retraction member self coils, the vascular device has a second overall length less than the first overall length.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Referring now in detail to the drawings where like reference numerals identify similar or like components throughout the several views, the device is designated generally by reference numeral 10 and is expanded to engage the internal wall of the vessel and contracted to pull the vessel walls radially inwardly in the manner disclosed in U.S. Pat. No. 6,676,698, the entire contents of which is incorporated herein by reference.

Figure 1:
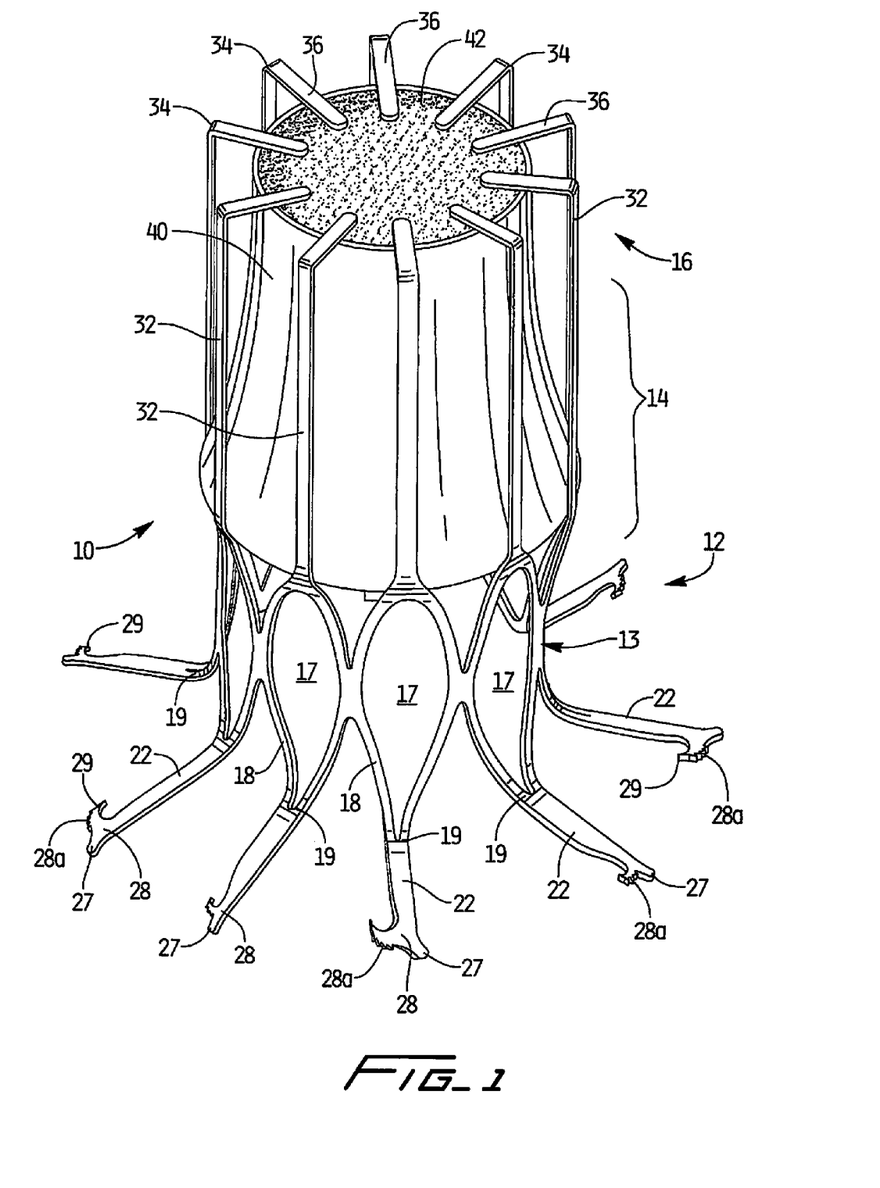
FIG. 1 is a perspective view of a first embodiment of the vascular device of the present invention shown in the expanded configuration.
Figure 2:
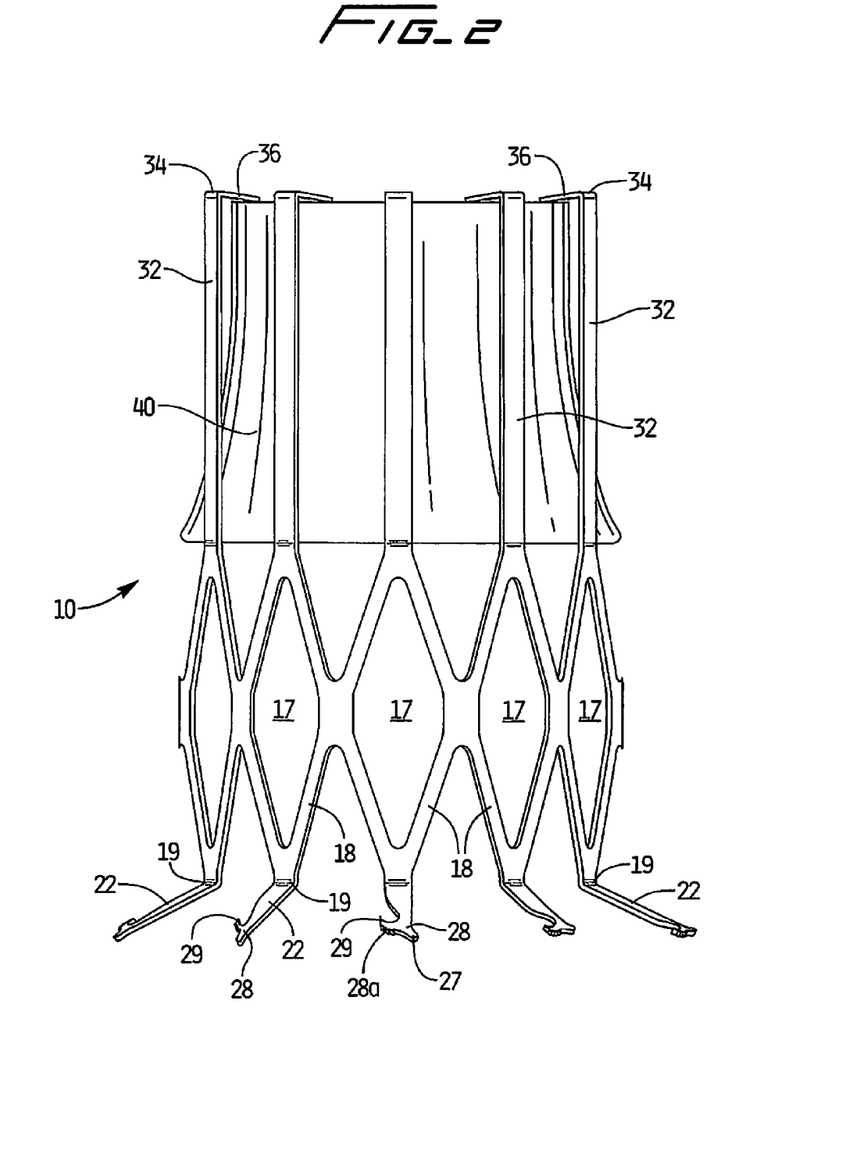
FIG. 2 is a side view of the vascular device of FIG. 1.

FIGS. 1 and 2 illustrate vascular device 10 of a first embodiment of the present invention in the expanded configuration. Vascular device 10 is preferably composed of a shape memory material, such as a nickel-titanium alloy, e.g. Nitinol, so that in its memorized configuration it assumes the shape shown in FIG. 1. This shape memory material characteristically exhibits rigidity in the austenitic state and more flexibility in the martensitic state. To facilitate passage from the delivery catheter, in one embodiment, the shape memory device is maintained in a collapsed configuration inside a delivery sheath where it is cooled by a saline solution to maintain the device below its transition temperature. The cold saline maintains the temperature dependent device in a relatively softer condition as it is in the martensitic state within the sheath. This facilitates the exit of device 10 from the sheath as frictional contact between the device and the inner wall of the sheath would otherwise occur if the device was maintained in a rigid, i.e. austenitic, condition. When the device 10 is released from the sheath to the target site, it is warmed by body temperature, thereby transitioning in response to this change in temperature to an austenitic expanded condition.

Device 10 is preferably formed from a tubular member, preferably by laser cutting. Device 10 includes a proximal portion 12, an intermediate portion 14 and a distal portion 16. In the expanded condition, at the proximal portion 12, the body 13 of device 10 includes struts 18 forming curved somewhat diamond shaped cells forming curved substantially diamond shaped openings 17. The proximal end regions 19 of the cells 18 extend into struts 22 bent outwardly from the plane of the remainder of the cell, in a direction away from the longitudinal axis of the vascular device 10. This better enables the vessel engaging members, described below, to engage the vessel walls. Although shown bent at close to a 90 degree angle, other angles are contemplated. For clarity, not all the identical parts in the views are labeled.

A vessel engaging member 28 is formed at the end of each strut 22. The member 28 is in the form of a hook having a penetrating tip 29 to pierce the vessel wall. That is, the struts 22 terminate in hooks 28. Hooks 28 include a series of teeth 28a to engage the vessel wall to provide additional retention to prevent movement of the device 10. A heel 27 extends past the hook to function to limit penetration of the strut portions through the vessel wall. This hook configuration is described in detail in commonly assigned co-pending patent Publication No. 2007/012368 (Ser. No. 11/801,547, filed Jul. 30, 2006), the entire contents of which are incorporated herein by reference.

The sharp penetrating tips 29 penetrate the vessel wall in a radial direction and hold the vessel against axial movement with respect to the device 10, and restrict radial movement with respect to the device 10, thereby together securely retaining (grasping) the vessel wall for radial inward movement described below.

It should be understood that fewer or greater number of vessel engaging members as well as different engaging structures can be provided as long as they achieve the vessel retaining function described herein.

When the vascular device 10 expands, struts 22 are moved to a shape memorized orientation bent outwardly at an angle, preferably about 90 degrees, with respect to the longitudinal axis of the device 10 with regions 19 bending out of the plane to increase the distance the members can extend from the center to the vessel wall. In the collapsed delivery position, struts 22 preferably lie substantially parallel to the struts 32 extending distally from the cells 18 and to the longitudinal axis of the device, with the hooks 28 also lying in the same plane to reduce the profile of the device for insertion. That is, in the delivery position, the struts 32 extend substantially parallel to the longitudinal axis of device 10 in the same way the struts 22 and hooks 28 are substantially parallel. Once released from the delivery sheath, they move to their memorized position shown in FIG. 1.

The intermediate portion 14 and distal portion 16 of the device 10 include the strut portions (elongated members) 32 extending longitudinally, alongside (external to) the valve 40. Struts 32 then bend inwardly at region 34, at for example a ninety degree angle, although other angles are contemplated, including more radiused bent regions, so strut portions 36 lie over a distal portion 42 of the valve 40 to secure the valve 40 to the device 10. The expanded placement position is shown in FIG. 1, with the struts 32 assuming their shape memory bent position.

Figure 4:
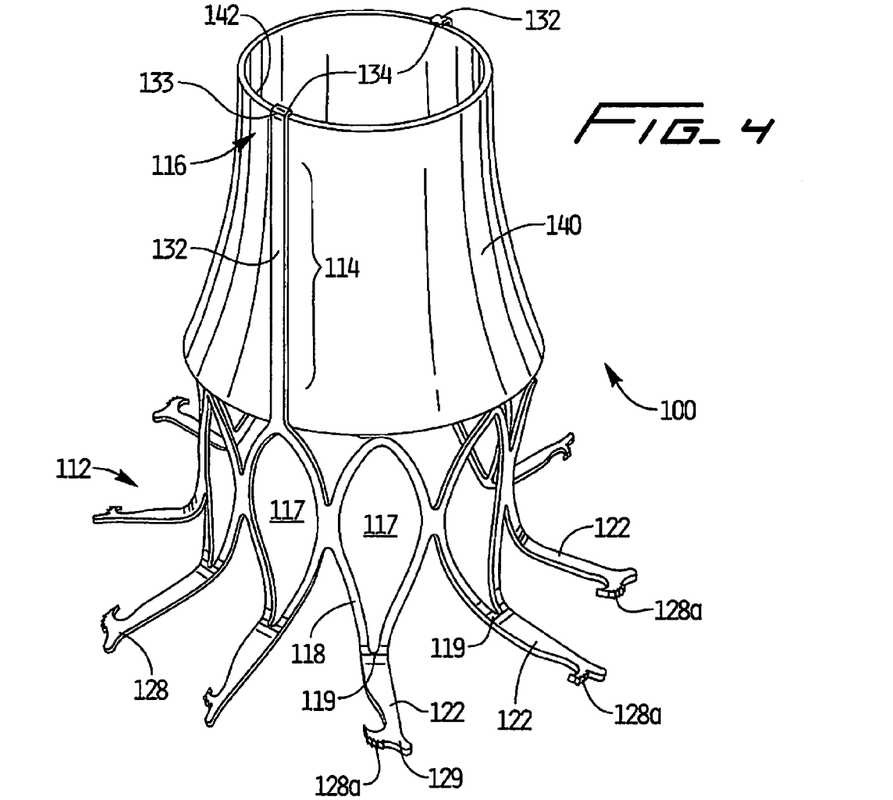
FIG. 4 is a perspective view of an alternate embodiment of the vascular device of the present invention shown in the expanded configuration.
Figure 5:
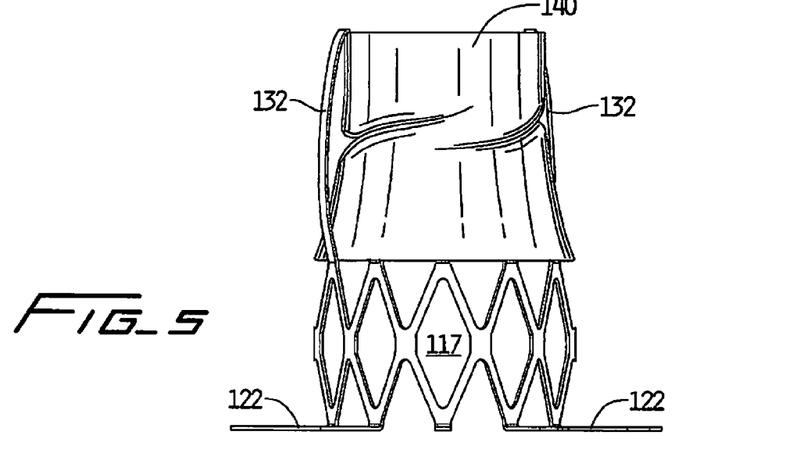
FIG. 5 is a side view of the vascular device of FIG. 4 with the valve partially collapsed.

An alternate embodiment of the vascular device is illustrated in FIGS. 4 and 5 and designated generally by reference numeral 100. Device 100 has a proximal portion 112 identical to the proximal portion 12 of FIG. 1, with identical parts labeled in the '100 series. Device 100 differs from device 100 in the intermediate portion 114 and distal portion 116. These portions 114, 116 include two strut portions (elongated members) 132 extending longitudinally from the cell struts 118, alongside an external surface of the valve 140. Preferably there are two strut portions 132, spaced approximately 180 degrees apart, however, a different spacing and a different number of strut portions 132 could be provided. The strut portions 132 terminate in ends 134 extending inwardly at region 133, at for example a ninety degree angle, although other angles are contemplated, including more radiused bent regions, so that strut portions 134 lie over a distal edge 142 of the valve 140 to secure the valve 140 to the device 100. Thus, elongated strut members 134 form a retaining hook to retain the valve. The strut portions can be fixed to the valve, enabling the valve to move between open and closed positions while still being retained. The strut portions 132 in one embodiment can flex to accommodate collapsing of the valve, as shown for example in FIG. 5. The expanded placement position of device 100 is shown in FIGS. 4 and 5 with the struts 132 assuming their shape memory bent position. Note that the struts 122 (and 22) can be bent at angles other than those shown. Struts 122 lie substantially parallel to the longitudinal axis of the device in the collapsed delivery position.

There are several different methods of insertion of the vascular devices of the present invention for treating venous valve insufficiency of the popliteal or saphenous vein. These are disclosed in detail in the U.S. Pat. No. 6,676,698, showing for example placement into the popliteal vein in the patient's leg and advanced to a region adjacent the leaflets to deploy the vascular device upstream of the leaflets. The delivery catheter is explained in the U.S. Pat. No. 6,676,698 as delivered in an antegrade fashion, with the tip extending downstream of the leaflets to deploy the device just upstream (defined in reference to the direction of blood flow) of the leaflets.

The vascular devices can be inserted through the right jugular vein, where the device will be advanced through the superior and inferior vena cava, past the iliac vein, through the femoral vein and into the popliteal vein through leaflets in a retrograde fashion, i.e. opposite the direction of blood flow. The delivery catheter thus extends through the leaflet region just upstream of the leaflets. It alternatively can be placed in the right femoral vein, where it will be advanced in a retrograde manner to the popliteal vein. In the contralateral approach, it is inserted through the left femoral vein where it will be advanced around the iliac vein and through the left femoral vein into the popliteal vein.

In use in one method, the catheter or delivery sheath is inserted over a conventional guidewire (not shown) so the distal tip of the catheter shaft extends past, i.e. downstream, of the valve leaflets L extending annularly from vessel wall. As can be appreciated, since there is a gap between the valve leaflets, the valve cannot function properly because the leaflets cannot properly close to prevent backflow. Also, due to the malfunctioning of the valve, the vessel wall becomes dilated as the weight and pressure of the backflow blood pushes out the vessel wall.

Once the position of the sheath is confirmed by venography, intravascular ultrasound, or other means, the sheath is withdrawn with respect to catheter tip to expose the device 10 (100) so it is warmed by the body temperature and transitions to its austenitic phase and the first memorized expanded configuration of FIG. 1. Note that device 100 (and devices 200, 300, 400 and 500 described below) can be inserted in the same ways as device 10 and therefore reference to insertion of device 10 also contemplates inserting device 100.

Next, as described in the U.S. Pat. No. 6,676,698, the balloon member on the catheter shaft which is positioned within device is inflated via introduction of fluid through an inflation lumen to further expand the device 10 to a second expanded configuration. That is, the device is expanded to a larger diameter than the diameter in its memorized configuration of FIG. 1 so that vessel engaging members 28 will engage the vessel wall with the sharp tips 29 penetrating the vessel wall to firmly grasp and secure it. This securement restricts both radial and axial movement of the vessel to enhance retention by the device 10.

After retention of the vessel wall, the balloon is deflated (and the catheter removed), resulting in the device 10 contracting from the second expanded configuration towards its memorized configuration. Preferably, the device 10 will return to substantially the same diameter as the first (memorized) expanded configuration. As contracted, the device 10, due to the engagement of the vessel engaging members with the internal wall of the vessel, pulls the vessel wall radially inwardly. As can be appreciated, the vessel wall is no longer dilated and sufficiently approximated for proper functioning of the replacement valve as the device 10 remains inside the vessel.

Figure 3A:
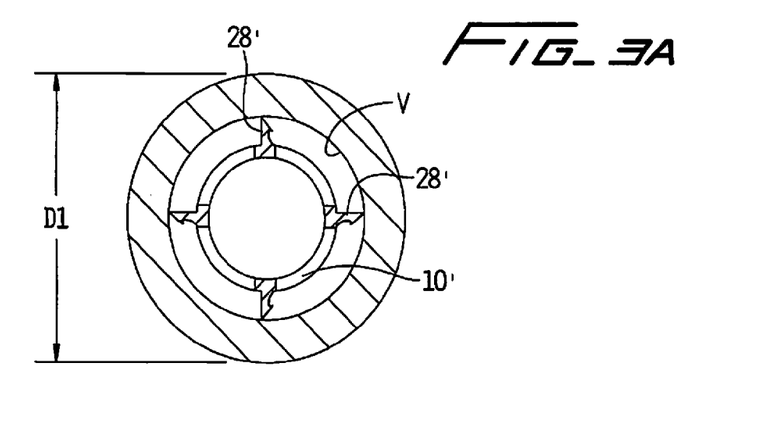
FIGS. 3A-3C are transverse cross-sectional views of the vascular device of FIG. 1 showing its interaction with the vessel wall during delivery and placement.
Figure 3B:
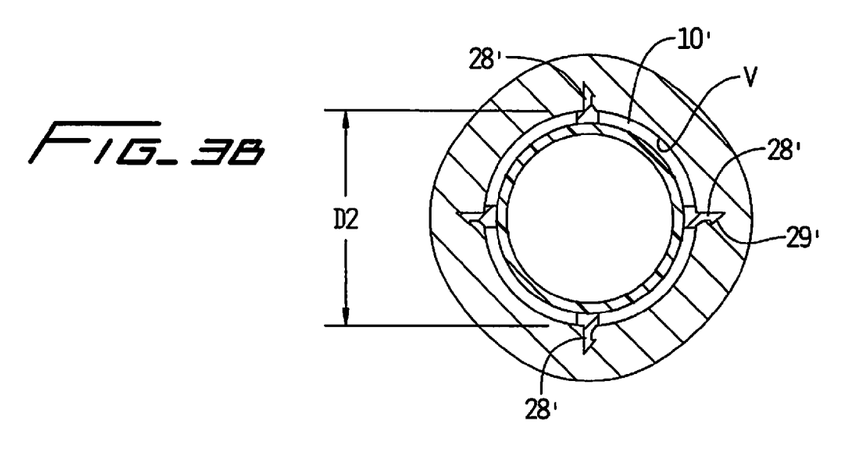
Figure 3C:
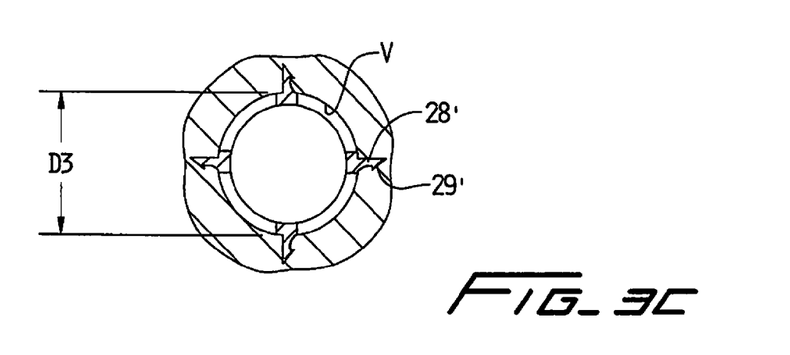

The changing diameters of the vascular device 10 can also be appreciated by reference to the transverse cross-sectional views of FIG. 3A-3C which show vascular device 10' with hooks 28' different than hooks 28 of FIG. 1. (Vascular device 100 would also have changing diameters like device 10). The delivery device has been removed for clarity. More specifically, FIG. 3A corresponds to the initial position of the vascular device 10' wherein the device 10' has been delivered to the target vessel, and has expanded to the first expanded (memorized) configuration but the vessel engaging members have not penetrated the vessel wall. It should be appreciated that in this configuration, the vessel engaging members may or may not be in contact with the vessel wall, but in either case, do not fully penetrate and secure the vessel to the same extent as in the second position. As shown, by way of example, the unhealthy dilated vessel can have an internal diameter D1 of approximately 14 mm. The balloon is not shown in FIG. 3A for clarity.

FIG. 3B corresponds to the position of the vascular device wherein the balloon has been inflated to radially expand the device 10' to a second expanded position to enable the vessel engaging members to penetrate and retain (secure) the vessel wall. In this configuration, the vessel wall is further expanded for example, to a diameter D2 of about 16 mm, as the device is expanded to a diameter of about 16 mm, with the hooks extending an additional 2 mm so the device is expanded to 20 mm.

FIG. 3C corresponds to the position of the vascular device 10' wherein the balloon has been deflated and the device contracted to bring the vessel wall radially inwardly. The internal vessel wall diameter will preferably be about 12 mm. The diameter of the vascular device 10' preferably returns to the same diameter as in FIG. 3A, e.g. about 12 mm. As can be seen the device 10' abuts the vessel wall V.

Note these dimensions are provided by way of example as other dimensions are also contemplated.

The vascular device 10 (and 100) can also be placed downstream (with respect to the direction of blood flow) of the valve leaflets. The delivery catheter is inserted in the same antegrade manner as described above, except it is advanced sufficiently past the valve leaflets L to enable downstream delivery of the device 10 (100). The device 10 (100) would grasp the vessel wall downstream of the valve leaflets to pull the vessel wall radially inwardly to bring the leaflets into apposition.

Figure 10:
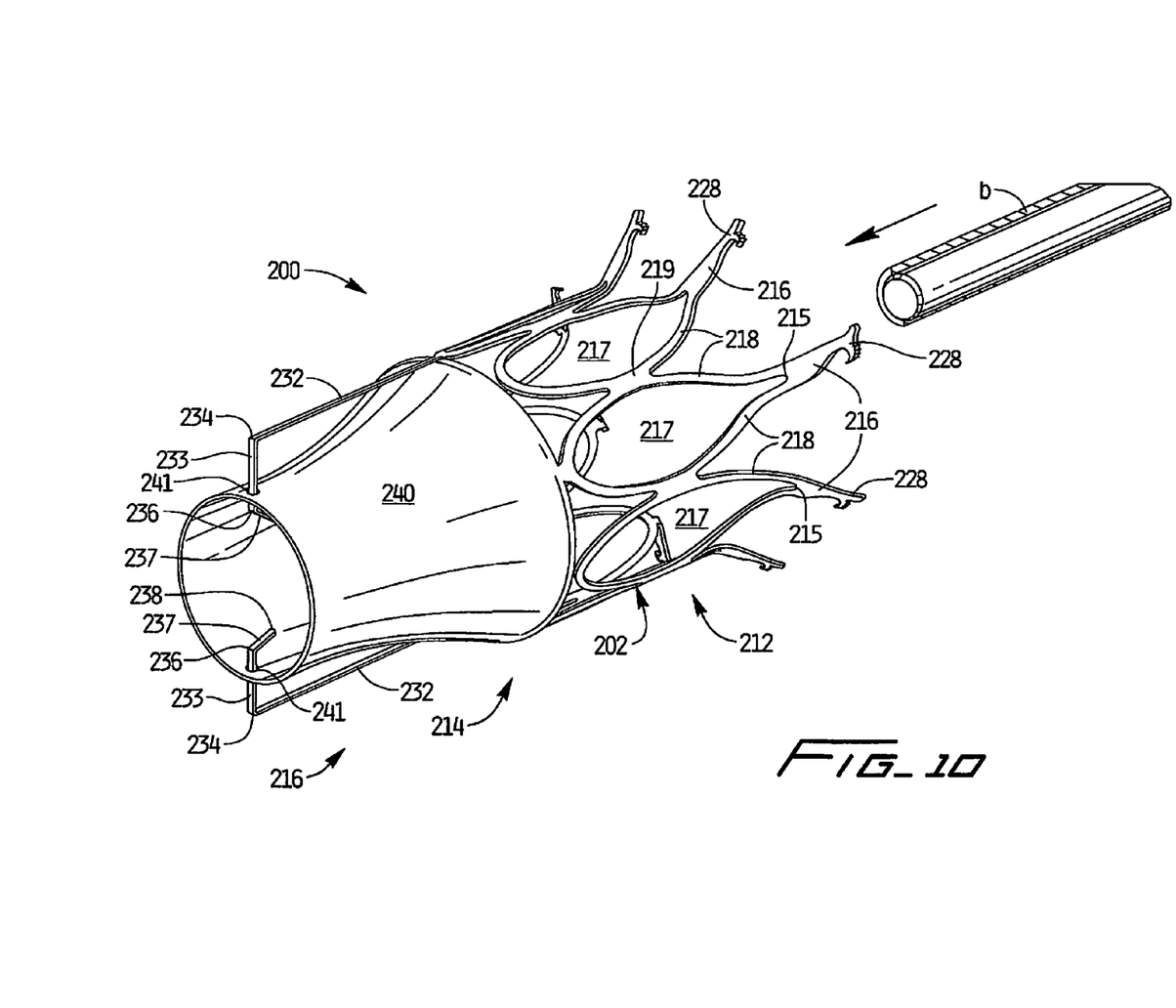
FIG. 10 is a perspective view of the vascular device of FIG. 6 shown fully deployed from the sheath and in the expanded configuration.

Turning now to FIGS. 6-10, an alternative embodiment of the vascular device is illustrated and configured for low profile insertion. With reference first to FIG. 10, vascular device 200 has a proximal portion 212, intermediate portion 214 and distal portion 216. These portions 214, 216 include two elongated struts (or strut portions) 232 extending longitudinally from the proximal portion 212, alongside (external of) the valve 240, preferably substantially parallel to the longitudinal axis of the valve 240. Preferably, two elongated strut members 232 are provided, spaced approximately 180 degrees apart; however, a different spacing and a different number of struts 232 could be provided. The vessel engaging members (or hooks) 228 are illustratively identical to the vessel engaging members 28 of FIG. 1 and for brevity their description is not repeated herein. As with hooks 28, the hooks 228 are preferably provided in alternating small and larger size to enable nesting to reduce the profile for insertion.

As shown in FIG. 10 illustrating the expanded condition of the vascular device 200, the struts 232 extend longitudinally along and external to the valve 240 and bend inwardly at region 234, preferably at an angle of about 90 degrees but other angles are also contemplated, to form radial portion 233. Radial portion 233, extending substantially transversely to the longitudinal axis of the valve 240, then bends inwardly at region 236 forming angled portion 237 terminating in blunt tip 238. The angle shown is an obtuse angle but other angles are also contemplated. As shown, the valve 240 includes two spaced apart openings 241 to accommodate passage of the radial portion 233 of the struts 234 to secure the valve to the struts 232. Additional openings can be provided to accommodate additional struts if provided. The engagement with the openings 241 fixes the struts to the valve 240, enabling the valve to move between open and closed positions while still being retained. The expanded placement position of device 200 is shown in FIG. 10 with the struts 232 assuming their shape memory bent position. Note that the struts 232 can be configured to bend at angles other than those shown.

Device body 202 is substantially identical to that of the embodiment of FIG. 4, having for example, curved diamond-like closed cells 217 formed by struts 218. Adjacent cells 217 are joined at region 219. For clarity, not all identical parts are labeled. The proximal end regions 215 of the cells 217 extend into struts 216 bent outwardly from the plane of the remainder of the cell, in a direction away from the longitudinal axis of the vascular device 200, and terminating in vessel engaging hooks 228.

Figures 8, 9:
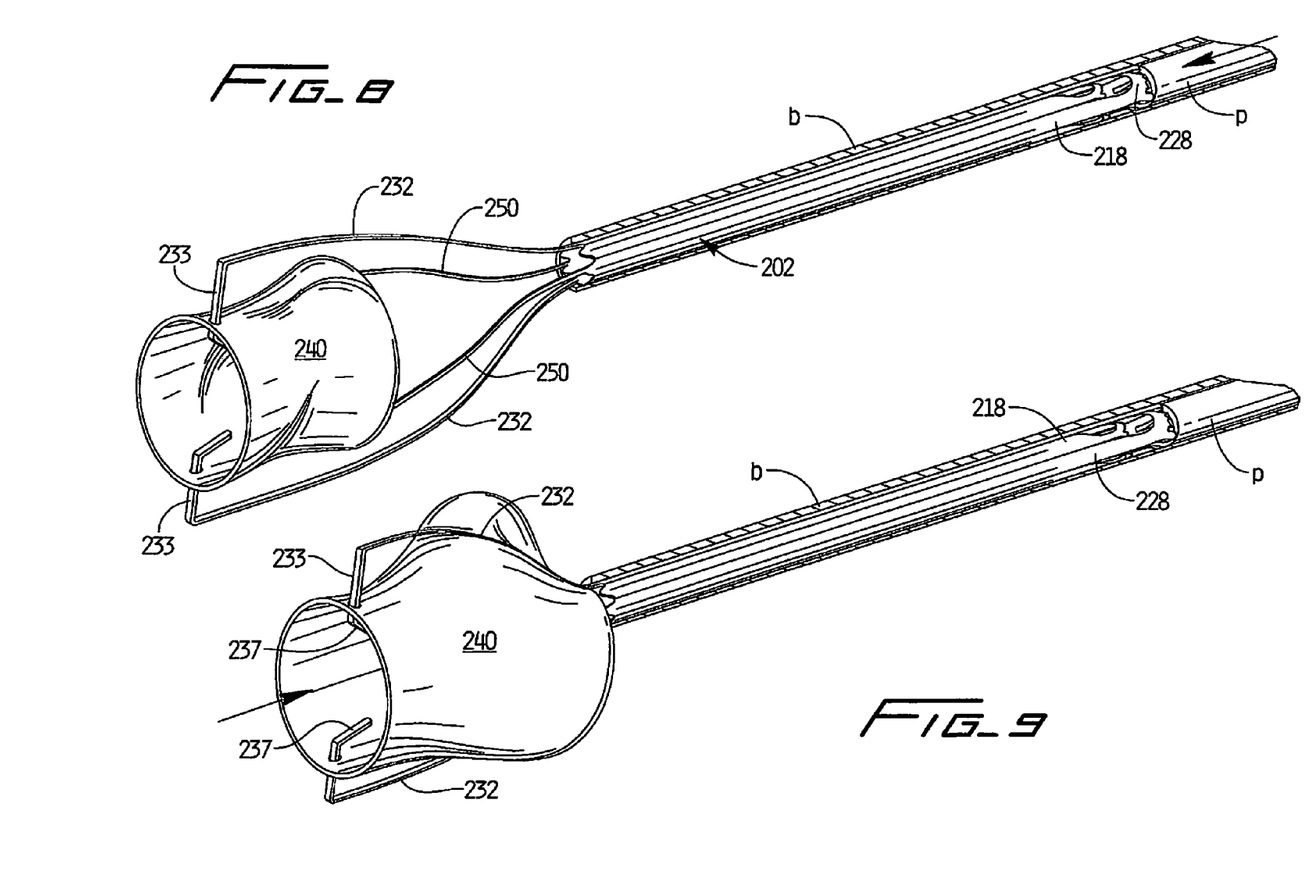
FIG. 8 is a perspective view similar to FIG. 7 showing the vascular device further deployed from the delivery sheath.
FIG. 9 is a perspective view similar to FIG. 8 showing the valve of the vascular device pulled proximally.

With reference to FIG. 8, wires 250 extend from a distal end of body 202. That is, the wires extend distally from the distal end of the cells 217. The wires extend distally within the delivery sheath D, and are attached to a proximal end of the valve 240. The wires 250 are preferably made from shape memory material with a shape memorized expanded position to pull the valve in a proximal direction upon delivery as discussed in detail below. The wires can also form a ring shaped configuration in the placement configuration, with its rim positioned transverse to a longitudinal axis of the valve 240, to apply a radial force against the valve 240 to help retain it in the lumen. In an alternate embodiment, a separate ring (not shown) is provided which would be in an elongated position for delivery to the vessel and then expands to a ring shape in the placement position. Although two wires are shown, it is also contemplated that a different number of wires could be provided.

Figures 6, 7:
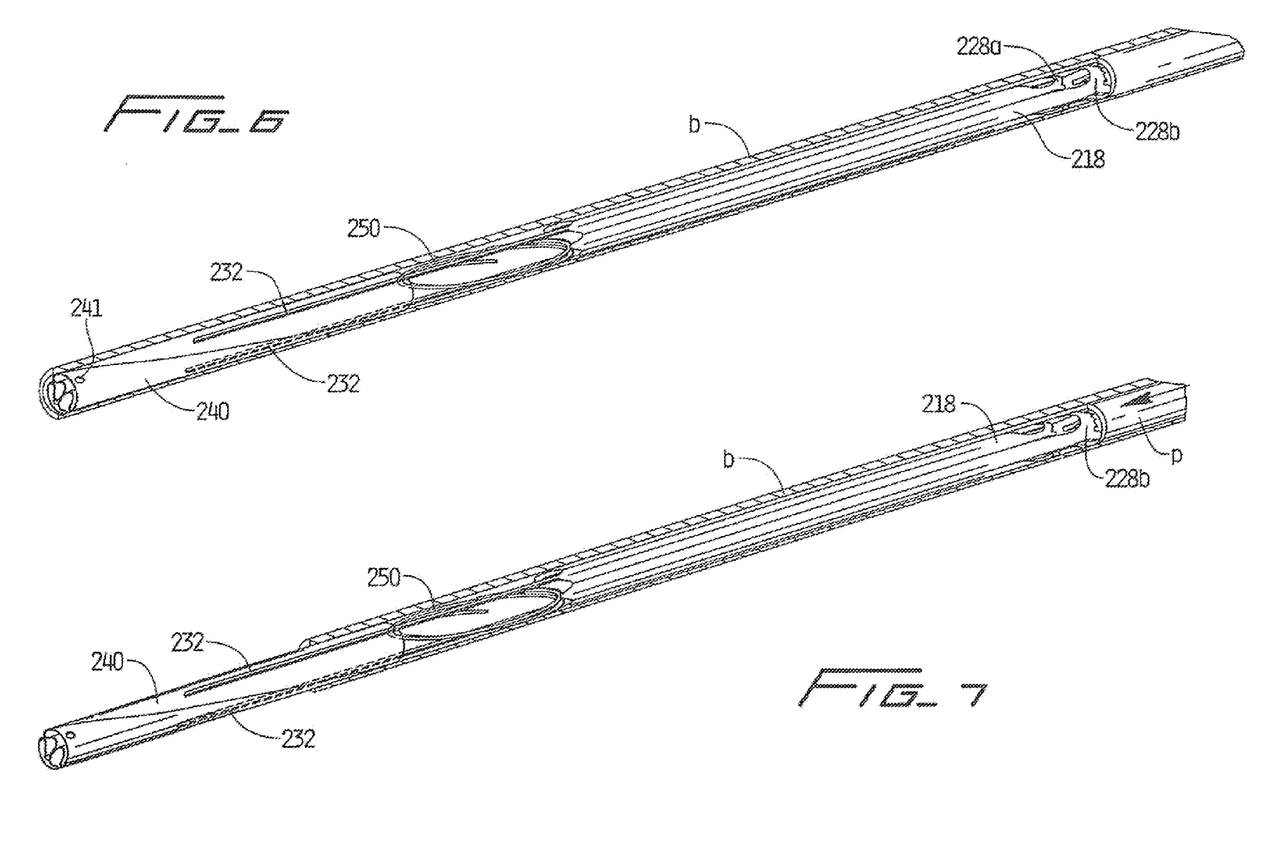
FIG. 6 is a perspective view of another alternate embodiment of the vascular device of the present invention shown in the collapsed position within a delivery sheath.
FIG. 7 is a perspective view similar to FIG. 6 showing the vascular device partially deployed from the delivery sheath.

The vascular device 200 is configured to minimize the insertion profile. To achieve this, the components of the device are aligned along a longitudinal axis during delivery. More specifically, as shown in FIG. 6, the struts of the proximal portion 212 of the device 200 are substantially parallel in the collapsed position, with the vessel engaging members (hooks) 228 staggered so smaller hooks 228a nest within larger hooks 228b. Distal of the ring 250 in the delivery position is the valve 240 in the collapsed position. Wires 250 are in a collapsed coiled condition, positioned between the distal end of the closed cell region of the body 202 and the proximal end of the valve 240, attached at one end to the body 202 and the other end to the valve 240.

In use, the device 200 is inserted within sheath D in the position shown in FIG. 6. Once at the desired location, pusher P is advanced distally within delivery sheath D against the end of the device 200 in the direction of the arrow of FIG. 7, advancing the device 200 distally from the sheath, with the valve 240 being the first component exposed. FIG. 8 illustrates the valve 240, elongated struts 232 and wires 250 exposed from the sheath just before the wires recoil. That is, once the wires 250 are exposed, they self coil, pulling the valve 240 in a proximal direction within the space between the expanded struts 232. Thus, as shown the overall length of the device 200 is now less in the expanded placement position than in the delivery position due to the proximal movement of the valve 240. In one embodiment, the wires 250 returns to a ring shape to apply a radial force against the valve 240.

As the valve 240 is pulled proximally, radial portions 233 of struts 232 pass through the respective openings 241 in the valve 240 thereby securing the valve to the struts 232. FIG. 9 illustrates the valve pulled proximally by the coiling of the wires 250. Further advancement of the device 200 exposes the body 202, allowing the struts 218 and 216 to expand to the placement configuration of FIG. 10, forming cells 217 with the hook regions extending at an angle to the struts 218 in a similar manner as the embodiment of FIG. 4.

Figure 11:
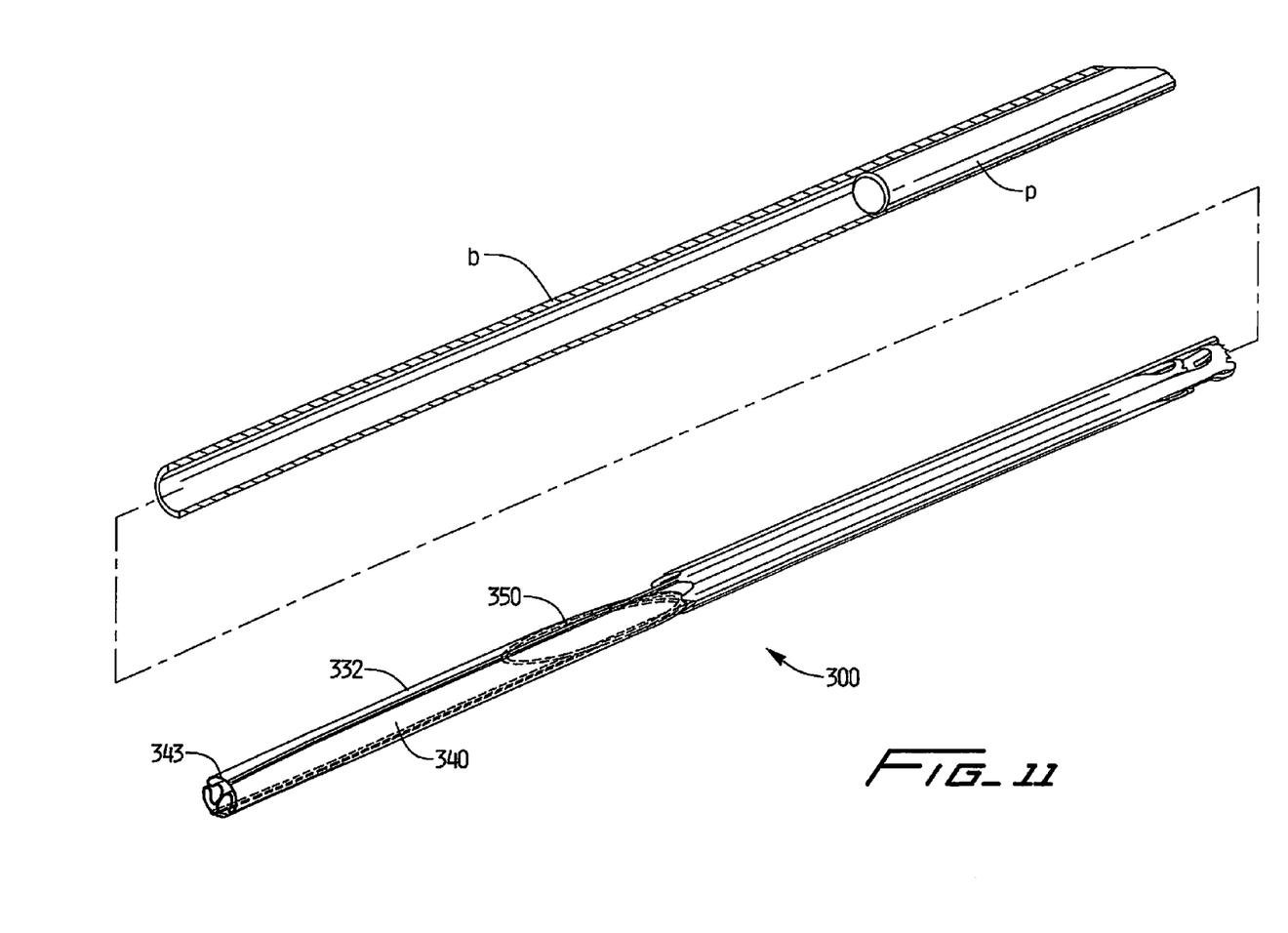
FIG. 11 is a perspective view of another alternate embodiment of the vascular device of the present invention shown in the collapsed position.
Figure 12:
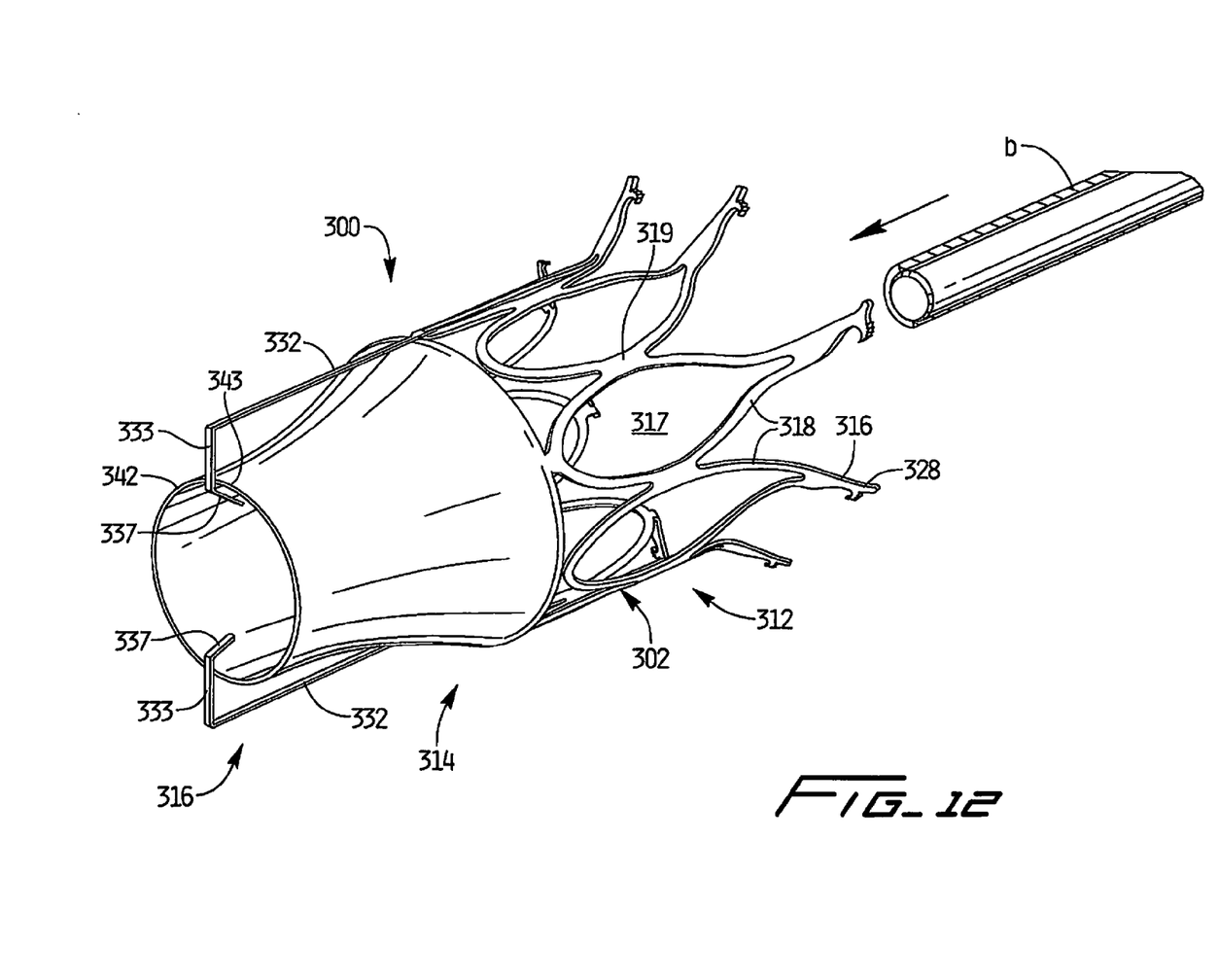
FIG. 12 is a perspective view of the vascular device of FIG. 11 shown fully deployed from the sheath and in the expanded configuration.

An alternate embodiment is illustrated in FIGS. 11 and 12. The vascular device is similar to the vascular device 300 of FIG. 6 except for the position of the shape memory wires 350 and elongated strut portions 332 during delivery and the cooperation of the end of the strut portions 332 and the valve 340. Body portion 302 of device 300 is identical to body portion 202 of device 200, with identical parts labeled in the '300 series, and therefore its structure, e.g. cells 317, struts 318 and 316 and vessel engaging members 328 and function, for brevity are not discussed herein.

Turning to the differences of vascular device 300 from device 200, the wires 350 are contained within the valve 340 during delivery. Also, the longitudinally extending struts 332 extend to a distal end 343 of the valve 340 during delivery. In this version, upon delivery, the valve 340 is not pulled proximally as in the embodiment of FIG. 6. Upon exposure from the sheath S, the valve 340 expands and the angled portions 337 extend from radial or transverse portions 333 of struts 332 are already positioned distal of the valve to prevent distal movement thereof. Moreover, as shown, the valve 340 is retained by the angled portions 337 of the struts 332, forming hook-like members extending over the distal edge (rim) of the valve 340 to retain the valve. Transverse portions 333 extend radially inwardly toward the longitudinal axis of the valve, at an angle of about 90 degrees, although other angles are clearly contemplated. Bent (angled) portions 337 extend at an obtuse angle to transverse portion 333, although other angles are contemplated. The distal edge 342 of the valve 340 is thus captured by the bent strut configuration of FIG. 12. As can be appreciated, struts 332 are unattached to the valve, but rely on the angles to retain the valve.

Figure 13:
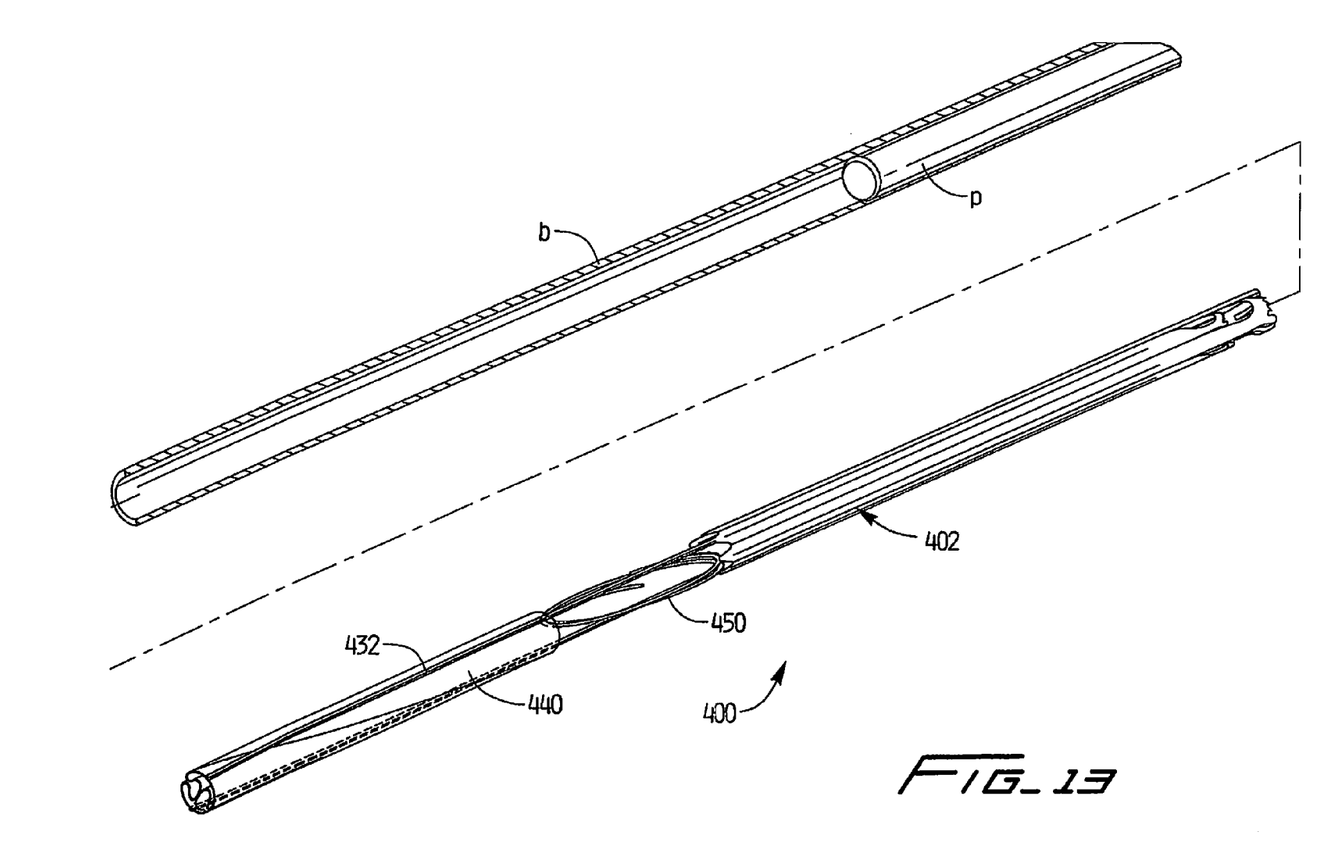
FIG. 13 is a perspective view of yet another alternate embodiment of the vascular device of the present invention shown in the collapsed position.

In the alternate embodiment of FIG. 13, in the insertion position, the wires 450 of vascular device 400 extend between a distal end of the body 402 and a proximal end of the valve 440 as in FIG. 6, however, the elongated strut portions 432 are positioned at the distal end of the valve 440. Upon delivery, the valve would expand within the confines of the bent portions of the struts 432 in the same manner as in FIG. 11. Except for the positioning of the wires 450 for delivery, the vascular device 400 is identical to the device 330 and therefore for brevity will not be discussed in further detail herein.

Figure 14:
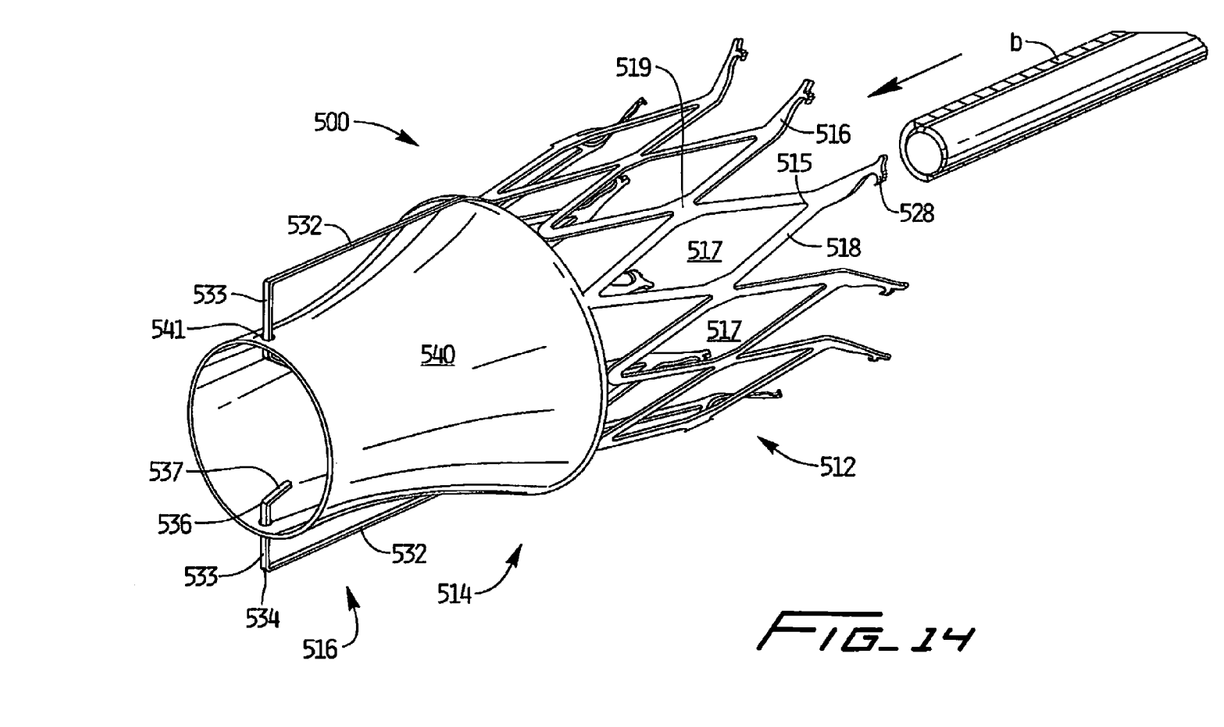
FIG. 14 is a perspective view of another alternate embodiment of the vascular device shown in the expanded configuration.

FIG. 14 illustrates an alternate embodiment of the vascular device, designated generally by reference numeral 500. Vascular device 500 is identical to device 200 of FIG. 6 except for the shape of the cells formed by the struts in the proximal region. As shown, the cells 517 are diamond shaped with struts 518 forming the boundary of the cell being substantially straight walls. The device engages the valve 540 in the same manner as valve 240 and is delivered and moves to its expanded operative position in the same manner as the device of FIGS. 6-10. For convenience, device 500 is labeled with reference numerals in the '500 series identical to the parts labeled with the '200 series in device 200 and for brevity these parts and their function are not repeated herein.

As an alternative to shape memory, a stainless steel or polymeric vascular device could be utilized. Such device would be expanded by a balloon below its elastic limit, thus enabling the device to return to its smaller configuration after the balloon is deflated. The vascular device could also be in the form of a braided structure which can be expanded to engage the vessel wall by squeezing or compressing its end (s), and then releasing it to enable it to return to its more elongated position of reduced diameter to approximate the vessel wall.

The vascular device is inserted in the vessel to expand and contract as described above, bringing the dilated vessel wall radially inwardly and leaving the replacement valve inside the vessel attached to the implanted vascular device. This replacement valve can be utilized as a total replacement wherein the patient's valve leaflets are removed, or can be placed upstream or downstream of the patient's leaflets, leaving the nonfunctioning leaflets in place. The valves can be attached at the proximal end, distal end, or intermediate the proximal and distal ends of the vascular devices.

Valve 40 is conically shaped as shown and is secured to the struts of the vascular device 10 and device 100 by various techniques. Other types of valves can be utilized such as those described in the U.S. Pat. No. 6,676,698.

A reinforcement ring could also optionally be provided. The valve can be multi-layered, with an outer layer composed of one material and an inner layer composed of another material.

The device can be repositioned by a grasper as described in the '698 patent. The valve can be attached to the vascular device by sewing, molding or other techniques. The valves can be composed of a variety of materials such as PET, PTFE, polycarbonate polyurethane, swine intestinal submucosa, collagen and other biomaterials. The valve and/or the vascular device surface can optionally be coated with anti-platelet or anti-thrombin/anti-clotting materials, 2b/2a coating, receptors, heparin coating, endothelial cell coating, etc.

While the above description contains many specifics, those specifics should not be construed, as limitations on the scope of the disclosure, but merely as exemplifications of preferred embodiments thereof. For example, instead of a balloon to expand the device to its second expanded diameter/condition, a mechanical means such as an expandable wire frame can be utilized. Also, instead of moving the sheath to expose the vascular device, the catheter can be advanced with respect to the sheath or both the catheter and sheath can move relative to each other in opposite directions. Those skilled in the art will envision many other possible variations that are within the scope and spirit of the disclosure as defined by the claims appended hereto.

What is claimed is:

1. A vascular device comprising:
a body formed from a tubular member and having a proximal portion and a distal portion and movable from a collapsed delivery position to an expanded placement position having a larger cross-sectional dimension, the body including a plurality of first struts forming a plurality of cells;
at least two elongated struts formed from the tubular member and integral with the first struts, the at least two elongated struts extending distally from the plurality of cells, and each elongated strut having a portion extending radially inwardly to extend transverse to a longitudinal axis of the device in an unconstrained position;
a plurality of vessel engaging members extending outwardly from the body for engaging the internal wall of a vessel; and
a valve movable between a collapsed delivery position and an expanded placement position, in the collapsed delivery position the valve spaced distally of the plurality of cells, at least a portion of the valve extending distally from a distal portion of the body in the placement position, wherein the elongated struts are positioned external of the valve and engage and lie over a distalmost edge of the valve in the placement position of the valve to retain the valve, the vessel engaging members positioned proximal of the valve, the valve engaged by the radially inwardly extending portions of the at least two elongated struts.

2. The vascular device of claim 1, wherein the vessel engaging members pull the internal wall of the vessel radially.

3. The vascular device of claim 2, wherein the body is composed of shape memory material and the expanded position substantially corresponds to a memorized position of the body, and the body is further expanded to a second expanded position by an expandable member.

4. The vascular device of claim 1, wherein in the collapsed position, the elongated struts extend external to at least a proximal portion of the valve.

5. The vascular device of claim 4, wherein the radially inwardly extending portions are at a distal end of the elongated struts and wherein in the collapsed position, the radially inwardly extending portions of elongated struts extend over an edge of a distal portion of the valve.

6. The vascular device of claim 1, wherein upon exposure of the valve from a delivery sheath, a portion of the valve is pulled proximally toward the body.

7. The vascular device of claim 1, further comprising an expandable ring positioned within the valve, wherein in the insertion position the ring is in a collapsed position.

8. The vascular device of claim 1, wherein the collapsed insertion position, the retraction member defines a loop positioned proximal and external of the valve.

9. A vascular device comprising:
a body having a proximal portion and a distal portion;
a valve extending distally from the body and having openings in a sidewall;
a retraction member connected to the valve and having a first longitudinal length in a first extended position and a second smaller longitudinal length in a second retracted position; and
at least two elongated struts extending radially inwardly and external of the valve;
wherein the body and valve are movable between a collapsed insertion position within a delivery sheath to an expanded placement position exposed from the delivery sheath, the body and valve having a larger cross-sectional dimension in the placement position than in the collapsed position, wherein upon exposure from the delivery sheath, the retraction member is movable in a proximal direction relative to the body from the first extended position for delivery to the second retracted position to apply a retraction force to the valve to pull the valve in a proximal direction such that the valve is closer to the body in the retracted position of the retraction member than in the extended position of the retraction member, wherein the elongated struts are out of engagement with the openings of the valve in the insertion position and are in engagement with the openings in the placement position.

10. The vascular device of claim 9, wherein the at least two elongated struts extend distally of the body, wherein the elongated struts are external to the valve as the valve is pulled proximally by the retraction member.

11. The vascular device of claim 10, wherein the elongated struts engage a distal portion of the valve to retain the valve.

12. The vascular device of claim 10, wherein a distal portion of the elongated struts extend radially inwardly toward a longitudinal axis of the valve.

13. The vascular device of claim 10, wherein at least one of the elongated struts is attached to the valve in the placement position.

14. The vascular device of claim 9, wherein the retraction member comprises at least one shape memory wire.

15. The vascular device of claim 9, further comprising an expandable ring contained within the valve, the expandable ring applying a radial force to the valve to force the valve against a vessel wall.

16. The vascular system of claim 9, wherein the body is composed of a shape memory material and is expandable first to a memorized condition in response to exposure to body temperature and subsequently expanded to the expanded position by an expandable member.

17. The method of claim 9, wherein in the retracted position the retraction member is a wire forming a ring shape to apply a radial force against the valve.

18. A method for treating venous valve insufficiency comprising:
inserting into a target vessel adjacent the region of the removed portion of valve leaflets a delivery device and a vascular device in an insertion position within the delivery device, the vascular device including a body, at least two elongated struts extending from the body, a plurality of vessel engaging members extending from the body, a valve, and a retraction member connected to the valve, wherein in the insertion position the body, retraction member and valve are in a reduced transverse dimensional configuration with at least a portion of the valve positioned distal of the body and the retraction member defines a loop in the insertion position, the loop is positioned between the body and the valve such that it is proximal and external of the valve in the insertion position; and exposing the vascular device from the delivery device, wherein when exposed the retraction member moves in a proximal direction relative to the body toward the vessel engaging members, from an extended position to a retracted position to move the valve in a proximal direction and when exposed the body expands to enable the vessel engaging members to engage the internal wall of the vessel, wherein in the retracted position of the retraction member the valve is closer to the body than in the extended position of the retraction member.

19. The method of claim 18, wherein in the insertion position, at least a portion of the retraction member is positioned proximal of the valve.

20. The method of claim 19, wherein in the insertion position the vascular device has a first overall length and after the retraction member self coils, the vascular device has a second overall length less than the first overall length.

* * * * *